United States Patent [19]
Sakurai et al.

[11] Patent Number: 5,668,623
[45] Date of Patent: Sep. 16, 1997

[54] CORNEAL SHAPE MEASURING APPARATUS

[75] Inventors: Akio Sakurai; Takeyuki Kato; Minoru Kamiya, all of Tokyo, Japan

[73] Assignee: Kabushiki Kaisha TOPCON, Tokyo, Japan

[21] Appl. No.: 276,465

[22] Filed: Jul. 18, 1994

[30] Foreign Application Priority Data

Jul. 16, 1993 [JP] Japan ................................. 5-176678

[51] Int. Cl.$^6$ ................................................. A61B 3/10
[52] U.S. Cl. ................................. 351/212; 351/205
[58] Field of Search ........................... 351/212, 247, 351/211, 219, 223, 224, 226, 222, 246, 205

[56] References Cited

U.S. PATENT DOCUMENTS

| | | | |
|---|---|---|---|
| 4,834,529 | 5/1989 | Barrett | 351/212 |
| 4,917,458 | 4/1990 | Matsumura | 351/247 |
| 4,998,819 | 3/1991 | Labinger et al. | 351/212 |

*Primary Examiner*—Hung X. Dang
*Attorney, Agent, or Firm*—Finnegan, Henderson, Farabow, Garrett & Dunner, L.L.P.

[57] ABSTRACT

A corneal shape measuring apparatus includes a system 1 for concentrically projecting a plurality of ring images 6 onto a cornea C, a system 3 for receiving the ring images 6 projected onto the cornea C, and a multipoint detecting circuit 9 and a light emission controlling circuit 10 each for avoiding the overlap of adjacent ring images of the ring images 6 projected onto the cornea C.

4 Claims, 6 Drawing Sheets

CORNEAL SHAPE MEASURING APPARATUS

BACKGROUND OF THE INVENTION

1. Field of the Invention

This invention relates to improvements in an apparatus for measuring a corneal shape by concentrically projecting a plurality of ring images onto a cornea.

2. Description of the Prior Art

Heretofore, a corneal shape measuring apparatus is known in which a plurality of ring images (for example, 10 to 30 ring images) are concentrically projected onto a cornea and then are received by a ring image receiving device to analyze distortions of the ring images formed on the cornea.

However, since the conventional apparatus is arranged to project the ring images onto the cornea at the same time, a case occurs in which adjacent ones of the ring images projected onto the cornea partly overlap with each other if the cornea is deformed. In such a case, an accurate measurement of the corneal shape cannot be taken by the conventional apparatus.

SUMMARY OF THE INVENTION

It is, therefore, an object of the invention to provide a corneal shape measuring apparatus capable of avoiding the overlap of data concerning adjacent ring images.

To achieve the object, the corneal shape measuring apparatus according to the invention comprises a ring image projecting system for concentrically projecting a plurality of ring images onto a cornea, a ring image receiving system for receiving the ring images projected onto the cornea, and a means for avoiding the overlap of data concerning adjacent ones of the ring images projected onto the cornea.

According to the corneal shape measuring apparatus, the overlap avoiding means avoids the overlap of the data concerning the adjacent ring images.

Preferably, the overlap avoiding means comprises a means for detecting the overlap of the data concerning the adjacent ring images and a means for, based on a detection result obtained by the detecting means, controlling the light emission of a ring image projecting light source in order to avoid the overlap.

Preferably, the light emission controlling means causes an odd-numbered ring image and an even-numbered ring image to be emitted individually.

The overlap avoiding means may comprise a ring image projecting system for concentrically and periodically projecting ring images having wavelengths different from each other onto the cornea, and an image receiving system for separating the ring images formed on the cornea by their wavelengths and receiving them. The wavelengths of the ring images vary in order from the innermost image to the outermost image.

Preferably, a two-dimensional image pickup element is used in the image receiving system. A color image pickup element can be used as the two-dimensional image pickup element.

A zoom optical system for projecting an enlarged or minified ring image onto the cornea can be used as the overlap avoiding means.

DETAILED DESCRIPTION OF THE PREFERRED EMBODIMENTS

Embodiments of a corneal shape measuring apparatus according to the invention will be hereinafter described with reference to the attached drawings.

Figure 1:
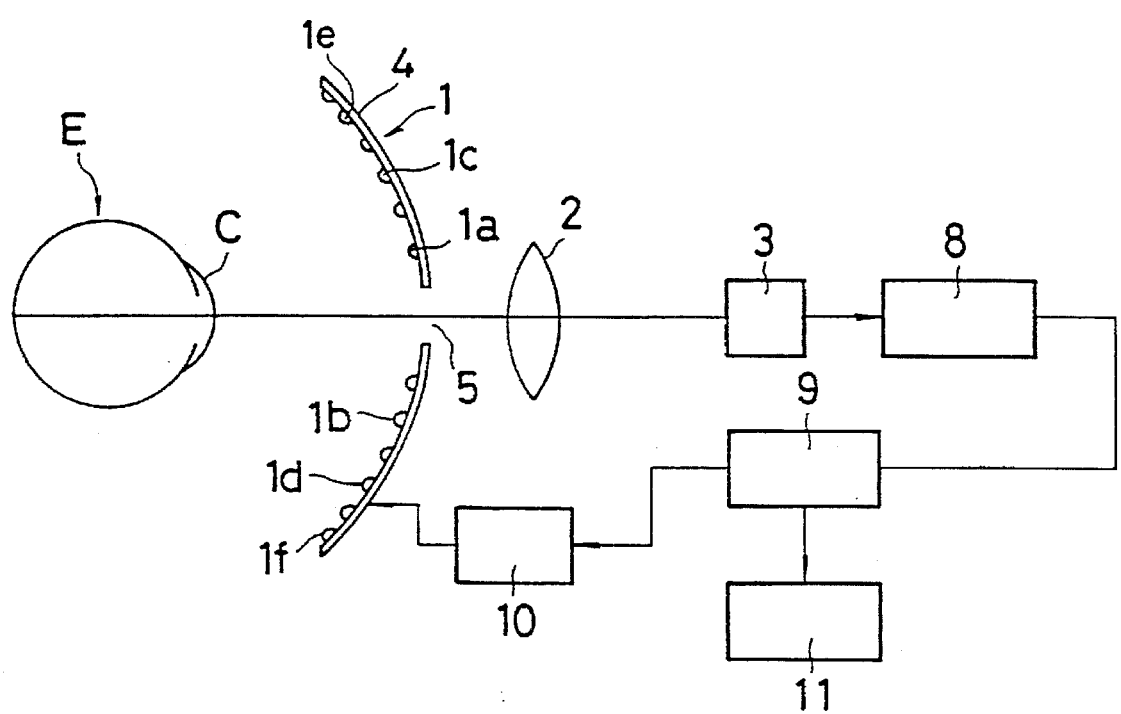
FIG. 1 is a schematic view showing a first embodiment of the corneal shape measuring apparatus according to the invention.
Figure 2:
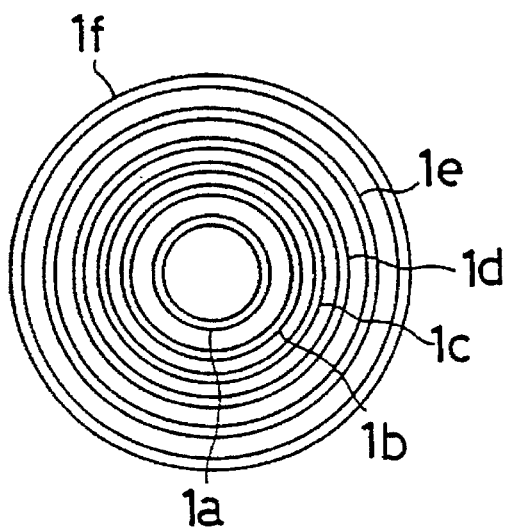
FIG. 2 is a plan view showing a ring image projecting source of FIG. 1.
Figure 3:
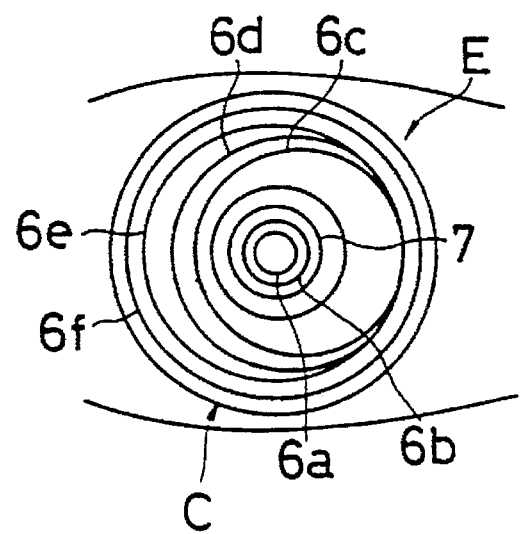
FIG. 3 shows a state of ring images formed on a cornea.

FIGS. 1 to 3 illustrate a first embodiment of the corneal shape measuring apparatus according to the invention.

Referring now to FIG. 1, E denotes a subject's eye, C denotes a cornea of the eye E, 1 denotes a ring image projecting light source, 2 denotes an image formation lens, and 3 denotes an image receiving element. As shown in FIG. 2, the light source 1 has concentric annular light sources $1a$ to $1f$. The annular light sources $1a$ to $1f$ are disposed on a curved plate 4 which has a circular opening 5 in its middle.

When the annular light sources $1a$ to $1f$ emit light at the same time, a plurality of ring images $6a$ to $6f$ are formed, as shown in FIG. 3, on the cornea C at the same time. Therefore, cases occur in which the ring images $6a$ to $6f$ are distorted according to the shape of the cornea C and consequently adjacent ones of the ring images $6a$ to $6f$ overlap. FIG. 3 shows a state of the overlap of the ring images $6c$, $6d$, and $6e$. The numeral 7 in FIG. 8 denotes the border of a pupil.

The ring images $6a$ to $6f$ are received by the image receiving element 3 shown in FIG. 1 through the image formation lens 2. The output of the image receiving element 3 is input to a binary circuit 8 and is transformed into a binary condition. The output of the binary circuit 8 is input to a multipoint detecting circuit 9. The multipoint detecting circuit 9 serves as a means for detecting the overlap of adjacent ones of the ring images $6a$ to $6f$ projected onto the cornea C. The multipoint detecting circuit 9 performs a process of transforming thick lines into thin lines which is adopted in the art of image processing. After that, the multipoint detecting circuit 9 judges whether the ring images overlap or not in the following manner. If a dot 13 which is located in the center of 3×3 masks is surrounded by two dots 14, 14 or less, as shown in, for example, FIGS. 9($a$)–9($e$) show the multipoint detecting circuit 9 judges that the ring images are not overlapping. If the dot 13 is surrounded by three dots or more, as shown in, for example, FIGS. 9($d$) and 9($e$), the multipoint detecting circuit 9 judges that the ring images are overlapping. That is, the multipoint detecting circuit 9 judges the overlap of the ring images by a state around the dot 13. This method is well known in the image processing art.

If the overlap of the adjacent ring images is detected, the multipoint detecting circuit 9 outputs a signal to a light emission controlling circuit 10. By the signal, the annular light sources 1a to 1f emit light alternately. For example, a group of the annular light sources 1a, 1c, and 1e emit light and thereby ring images 6a, 6c, and 6e, are formed respectively. Accordingly, the alternate ring images 6a, 6c, and 6e are projected onto the cornea C. These ring images 6a, 6c, and 6e are received by the image receiving element (image pickup element) 3 and, if the overlap of these images is not detected, data on the ring images 6a, 6c, and 6e are input to a measuring circuit 11. Next, a group of the annular light sources 1b, 1d, and 1f emit light and, through the same operations as in the above, data on the ring images 6b, 6d, and 6f are input to the measuring circuit 11. Therefore, based on the data on the ring images which are not overlapping, the measuring circuit 11 measures the shape of the cornea C.

That is, the multipoint detecting circuit 9 and the light emission controlling circuit 10 each serve as a means for avoiding the overlap of adjacent ones of the ring images 6a to 6f projected onto the cornea C.

In this embodiment, all of the annular light sources 1a to 1f emit light at the same time to detect the overlap of the ring images. Instead, the odd-numbered annular light sources 1a, 1c, and 1e may first emit light at the same time by means of the light emission controlling circuit 10 and then the even-numbered annular light sources 1b, 1d, and 1f may emit light at the same time by means of the circuit 10. As a result, data on two groups of ring images are input to the measuring circuit 11 to analyze the shape of the cornea C. In this case, since the overlap of adjacent ring images is prevented beforehand, the multipoint detecting circuit 8 is not used.

FIGS. 4 to 8 show a second embodiment of the corneal shape measuring apparatus according to the invention. In this embodiment, the same numerals are given to the same components as in the first embodiment and its description is omitted.

Figure 5:
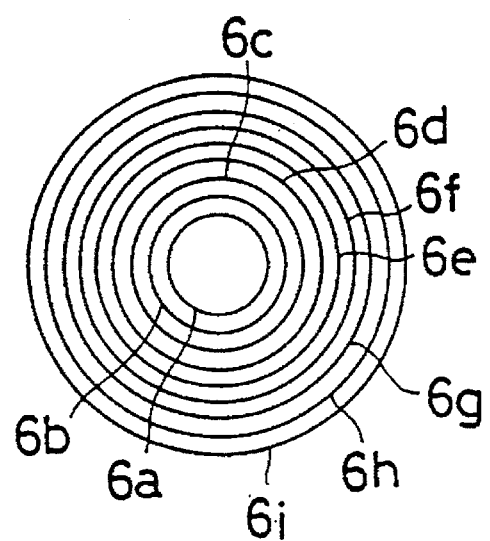
FIG. 5 shows a state of ring images formed on the cornea.

In the second embodiment, annular light sources 1a, 1d, and 1g are each a red light emitting source, annular light sources 1b, 1e, and 1h are each a green light emitting source, and annular light sources 1c, 1f, and 1i are each a blue light emitting source. Rays of light of the annular light sources 1a to 1i are emitted onto the cornea C at the same time. FIG. 5 shows ring images 6a to 6i projected onto the cornea C. The ring images 6a to 6i are formed concentrically and periodically. The wavelengths of the ring images 6a to 6i are different from each other in order from the innermost ring image 6a to the outermost ring image 6i.

Figure 4:
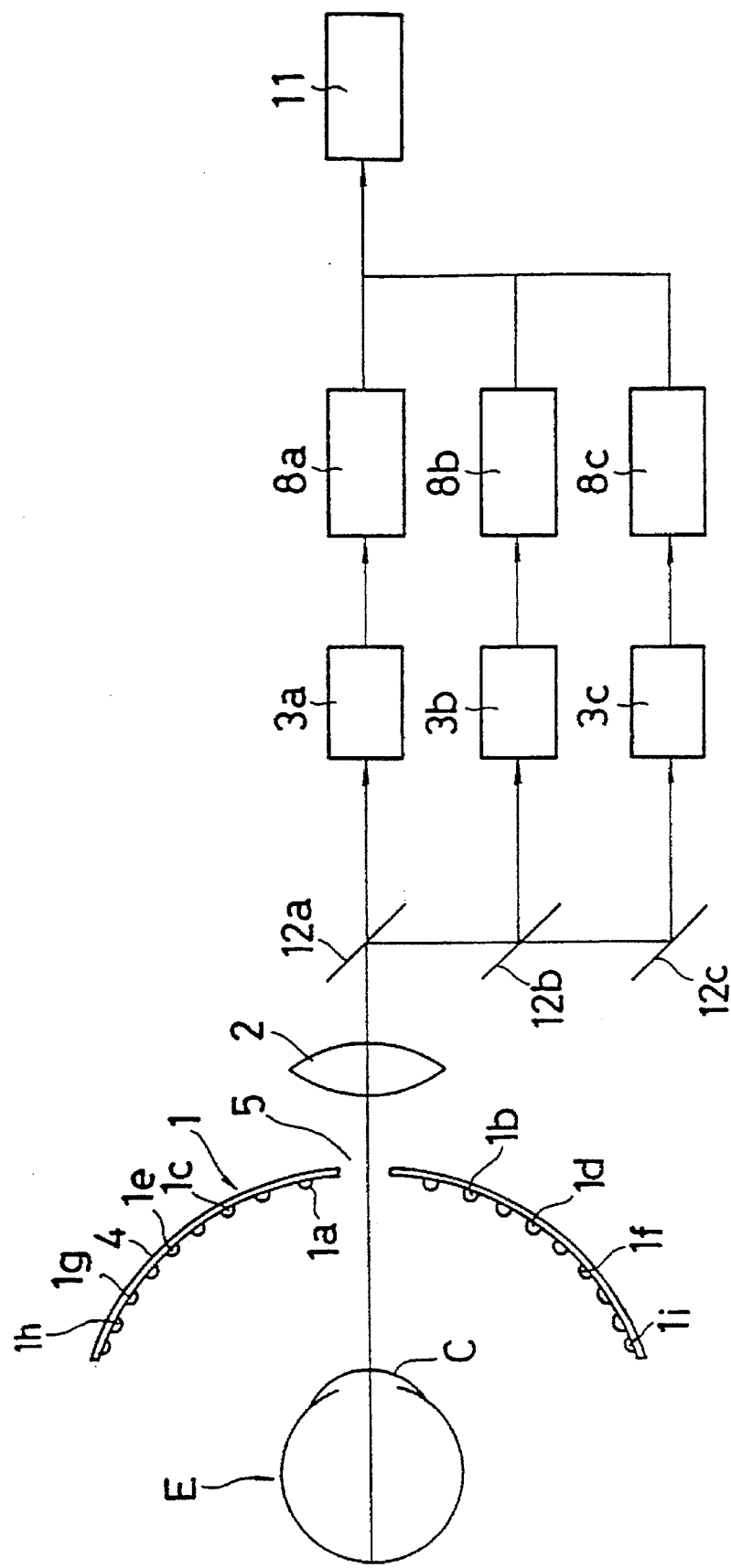
FIG. 4 is a schematic view showing a second embodiment of the corneal shape measuring apparatus according to the invention.

As shown in FIG. 4, a dichroic mirror 12a which transmits red light and reflect both green light and blue light is disposed in the optical path of the images formation lens 2. A dichroic mirror 12b which reflects the green light and transmits the blue light is disposed at a point in a direction in which the dichroic mirror 12a reflects the green light. A reflection mirror 12c which reflects the blue light is disposed at a point in a direction in which the dichroic mirror 12b transmits the blue light.

The red light which has passed through the dichroic mirror 12a is received by a light receiving element 3a. The green light reflected by the dichroic mirror 12b is received by a light receiving element 3b. The blue light reflected by the reflection mirror 12c is received by a light receiving element 3c.

Figure 6:
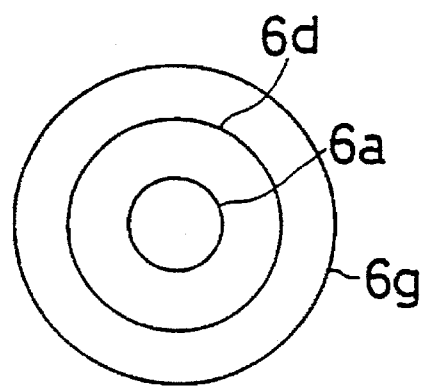
FIG. 6 shows a state in which ring images projected by a red color light source are formed on the cornea.
Figure 7:
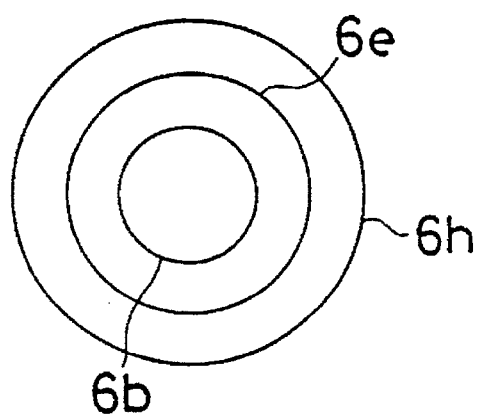
FIG. 7 shows a state in which ring images projected by a green color light source are formed on the cornea.
Figure 8:
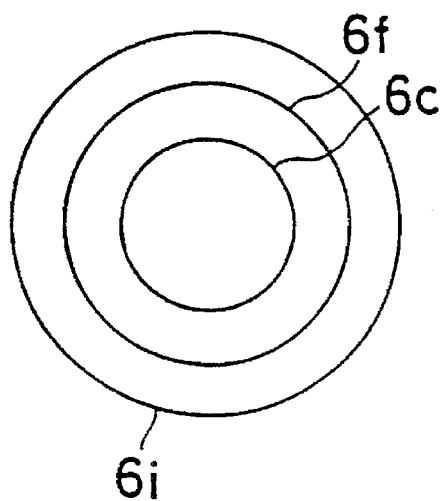
FIG. 8 shows a state in which ring images projected by a blue color light source are formed on the cornea.
Figure 9A:
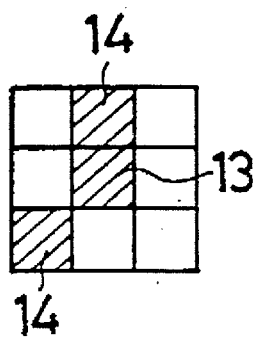
FIG. 9($a$)–9($e$) show examples of a judgment on whether ring images overlap with each other or not.
Figure 9B:
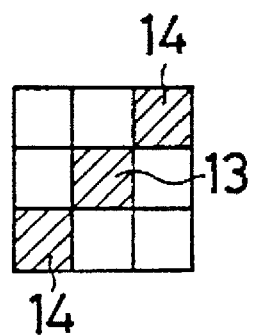
Figure 9C:
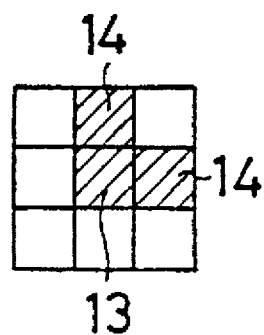
Figure 9D:
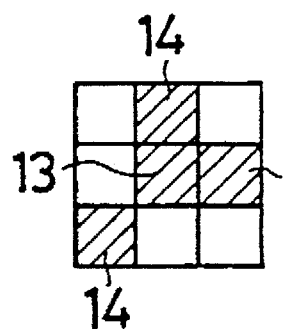
Figure 9E:
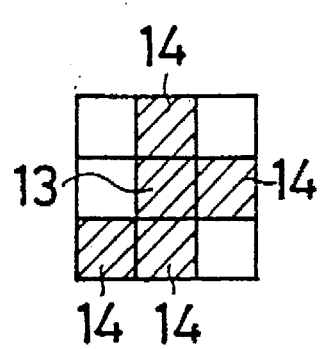

Therefore, as shown in FIGS. 6 to 8, a set of ring images 6a, 6d, and 6g are formed on the light receiving element 3a, a set of ring images 6b, 6e, and 6h are formed on the light receiving element 3b, and a set of ring images 6c, 6f, and 6i are formed on the light receiving element 3c. In each set of images, a large separation is obtained between the images. The output of the image receiving elements 3a to 3c is input to the measuring circuit 11 via the binary circuits 8a to 8c. Since the ring images of each set are received on the corresponding image receiving element without the overlap of adjacent ring images even if adjacent ring images formed on the cornea C overlap with each other, the measurements are made without any trouble. In this case, an optical path length of each wavelength is corrected so as to be focused.

In the second embodiment, the ring images formed on the cornea C are separated according to their wavelengths by means of the dichroic mirrors 12a, 12b and the reflection mirror 12c and are received by the corresponding elements. However, by the use of a color image pickup element (single-plate type or three-plate type) as the image receiving element 3, the ring images can be individually treated under a color separation process even if adjacent ones of the ring images overlap with each other.

Further, a plurality of ring images can be produced from a single ring image by enlarging and minifying the single ring image under a zoom projection method.

Since the corneal shape measuring apparatus according to the invention is arranged as mentioned above, the overlap of data concerning adjacent ring images can be avoided.

What is claimed is:

1. A corneal shape measuring apparatus comprising:

a ring image projecting system for concentrically projecting a plurality of ring images onto a cornea at the same time, said ring images each having the same wavelength;

a ring image receiving system for receiving the ring images projected on the cornea at the same time;

judgment means for judging whether or not the ring images are overlapped by analyzing the ring images received by said ring image receiving system; and control means for controlling light emission from light sources which project the ring images when the ring images projected on the cornea are overlapped so that the ring images projected on the cornea are not overlapped based on a judgment result obtained by said judgment means;

a shape of the cornea being measured based on the ring images received by said ring image receiving system through said judgment means and said control means.

2. A corneal shape measuring apparatus according to claim 1, wherein said control means individually controls light emission from odd-numbered light sources of said light sources and light emission from even-numbered light sources of said light sources.

3. A corneal shape measuring apparatus comprising:

a ring image projecting system for concentrically projecting a plurality of ring images onto a cornea at the same time, said ring images having wavelengths different from each other; and a ring image receiving system for receiving said ring images projected onto the cornea at the same time;

a shape of the cornea being measured based on the ring images received by said ring image receiving system.

4. A corneal shape measuring apparatus according to claim 3 wherein said ring image receiving system separates the ring images according to their wavelengths and receives the separated ring images.

* * * * *